(12) United States Patent
Jin et al.

(10) Patent No.: US 7,508,504 B2
(45) Date of Patent: Mar. 24, 2009

(54) AUTOMATIC WAFER EDGE INSPECTION AND REVIEW SYSTEM

(75) Inventors: Ju Jin, Austin, TX (US); Satish Sadam, Round Rock, TX (US); Vishal Verma, Austin, TX (US); Zhiyan Huang, Austin, TX (US); Siming Lin, Austin, TX (US); Michael D Robbins, Round Rock, TX (US); Paul F. Forderhase, Austin, TX (US)

(73) Assignee: Accretech USA, Inc., Bloomfield Hills, MI (US)

( * ) Notice: Subject to any disclaimer, the term of this patent is extended or adjusted under 35 U.S.C. 154(b) by 0 days.

(21) Appl. No.: 11/891,657

(22) Filed: Aug. 9, 2007

(65) Prior Publication Data

US 2008/0030731 A1 Feb. 7, 2008

Related U.S. Application Data

(63) Continuation-in-part of application No. 11/417,297, filed on May 2, 2006.

(51) Int. Cl.
*G01N 21/00* (2006.01)

(52) U.S. Cl. .............. 356/237.4; 356/237.2; 356/237.6; 356/417; 356/446

(58) Field of Classification Search ... 356/237.2–237.6, 356/417, 369, 446
See application file for complete search history.

(56) References Cited

U.S. PATENT DOCUMENTS

| | | | |
|---|---|---|---|
| 4,099,831 A | 7/1978 | Freeman | |
| 5,172,005 A * | 12/1992 | Cochran et al. | 356/430 |
| 5,461,417 A | 10/1995 | White et al. | |
| 5,629,607 A | 5/1997 | Callahan et al. | |
| 5,825,482 A | 10/1998 | Nikoonahad et al. | |
| 5,864,394 A | 1/1999 | Jordan, III et al. | |
| 5,883,710 A | 3/1999 | Nikoonahad et al. | |
| 5,912,735 A | 6/1999 | Xu | |

(Continued)

FOREIGN PATENT DOCUMENTS

EP   1 001 460 A   5/2000

(Continued)

OTHER PUBLICATIONS

Article printout from Micromagazine.com website entitled "Reducing Edge and Bevel Contamination to Help Enhance copper Process Yields" dated Oct. 2000.

(Continued)

*Primary Examiner*—L. G Lauchman
*Assistant Examiner*—Iyabo S Alli
(74) *Attorney, Agent, or Firm*—Harness, Dickey & Pierce, P.L.C.

(57) ABSTRACT

A substrate illumination and inspection system provides for illuminating and inspecting a substrate particularly the substrate edge. The system uses a light diffuser with a plurality of lights disposed at its exterior or interior for providing uniform diffuse illumination of a substrate. An optic and imaging system exterior of the light diffuser are used to inspect the plurality of surfaces of the substrate including specular surfaces. The optic can be rotated radially relative to a center point of the substrate edge to allow for focused inspection of all surfaces of the substrate edge.

25 Claims, 16 Drawing Sheets

U.S. PATENT DOCUMENTS

| | | | |
|---|---|---|---|
| 6,021,380 A * | 2/2000 | Fredriksen et al. | 356/390 |
| 6,081,325 A | 6/2000 | Leslie et al. | |
| 6,147,357 A | 11/2000 | Nicolesco | |
| 6,208,411 B1 | 3/2001 | Vaez-Iravani | |
| 6,215,551 B1 | 4/2001 | Nikoonahad et al. | |
| 6,217,034 B1 | 4/2001 | Smedt et al. | |
| 6,282,309 B1 | 8/2001 | Emery | |
| 6,369,524 B1 | 4/2002 | Sid | |
| 6,414,752 B1 | 7/2002 | Sullivan et al. | |
| 6,433,561 B1 | 8/2002 | Satya et al. | |
| 6,483,638 B1 | 11/2002 | Shafer et al. | |
| 6,525,883 B2 | 2/2003 | Hirohara et al. | |
| 6,538,375 B1 | 3/2003 | Duggal et al. | |
| 6,538,730 B2 | 3/2003 | Vaez-Iravani et al. | |
| 6,559,938 B1 | 5/2003 | Smedt | |
| 6,560,011 B2 | 5/2003 | Chuang et al. | |
| 6,578,961 B2 | 6/2003 | Vaez-Iravani | |
| 6,603,541 B2 | 8/2003 | Lange | |
| 6,608,676 B1 | 8/2003 | Zhao et al. | |
| 6,614,507 B2 | 9/2003 | Young et al. | |
| 6,614,520 B1 | 9/2003 | Bareket et al. | |
| 6,636,301 B1 | 10/2003 | Kvamme et al. | |
| 6,636,302 B2 | 10/2003 | Nikoonahad et al. | |
| 6,661,521 B1 | 12/2003 | Stern | |
| 6,661,580 B1 | 12/2003 | Solarz | |
| 6,674,522 B2 | 1/2004 | Krantz et al. | |
| 6,686,996 B2 | 2/2004 | Sullivan et al. | |
| 6,724,473 B2 | 4/2004 | Leong et al. | |
| 6,770,862 B1 | 8/2004 | Maciuca et al. | |
| 6,778,267 B2 | 8/2004 | Drake | |
| 6,781,688 B2 | 8/2004 | Kren et al. | |
| 6,791,680 B1 | 9/2004 | Rosengaus et al. | |
| 6,798,503 B2 | 9/2004 | Hiramoto et al. | |
| 6,801,358 B2 | 10/2004 | Shafer et al. | |
| 6,806,951 B2 | 10/2004 | Wack et al. | |
| 6,816,249 B2 | 11/2004 | Fairley et al. | |
| 6,816,251 B2 | 11/2004 | Swan et al. | |
| 6,820,349 B2 | 11/2004 | Peine | |
| 6,844,927 B2 | 1/2005 | Stokowski et al. | |
| 6,850,321 B1 | 2/2005 | Yu | |
| 6,862,142 B2 | 3/2005 | Lange | |
| 6,879,390 B1 | 4/2005 | Kvamme et al. | |
| 6,882,415 B1 | 4/2005 | Watkins et al. | |
| 6,888,627 B2 | 5/2005 | Leslie et al. | |
| 6,903,338 B2 | 6/2005 | Mankos et al. | |
| 6,906,794 B2 | 6/2005 | Tsuji | |
| 6,919,957 B2 | 7/2005 | Nikoonahad et al. | |
| 6,922,236 B2 | 7/2005 | Vaez-Iravani et al. | |
| 6,937,753 B1 | 8/2005 | O'Dell et al. | |
| 6,946,670 B1 | 9/2005 | Zurbrick | |
| 6,947,588 B2 | 9/2005 | Sim | |
| 6,985,220 B1 | 1/2006 | Chen et al. | |
| 6,999,183 B2 | 2/2006 | Nielsen et al. | |
| 7,001,055 B1 | 2/2006 | Lange | |
| 7,005,671 B2 | 2/2006 | Yamazaki et al. | |
| 7,009,696 B2 | 3/2006 | Sullivan et al. | |
| 7,012,683 B2 | 3/2006 | Wolf et al. | |
| 7,013,222 B2 | 3/2006 | Strader | |
| 7,019,717 B2 | 3/2006 | Yumoto et al. | |
| 7,038,771 B2 | 5/2006 | Smedt | |
| 7,038,772 B2 | 5/2006 | Chen et al. | |
| 7,038,773 B2 | 5/2006 | Kuhlmann et al. | |
| 7,046,355 B2 | 5/2006 | Yu | |
| 7,068,363 B2 | 7/2006 | Bevis et al. | |
| 7,072,034 B2 | 7/2006 | Rosengaus et al. | |
| 7,075,637 B2 | 7/2006 | Leslie et al. | |
| 7,079,237 B2 | 7/2006 | Woo et al. | |
| 7,079,238 B2 | 7/2006 | Vaez-Iravani et al. | |
| 7,088,443 B2 | 8/2006 | Vaez-Iravani et al. | |
| 7,092,082 B1 | 8/2006 | Dardzinski | |
| 7,126,681 B1 | 10/2006 | Chen et al. | |
| 7,130,036 B1 | 10/2006 | Kuhlmann et al. | |
| 7,130,039 B2 | 10/2006 | Vaez-Iravani et al. | |
| 7,136,234 B2 | 11/2006 | Shafer et al. | |
| 7,161,667 B2 | 1/2007 | Meeks et al. | |
| 7,161,668 B2 | 1/2007 | Meeks et al. | |
| 7,161,669 B2 | 1/2007 | Velidandla et al. | |
| 7,164,475 B2 | 1/2007 | Fairley et al. | |
| 7,199,946 B2 | 4/2007 | Jeong | |
| 7,209,227 B2 | 4/2007 | Smedt | |
| 7,218,391 B2 | 5/2007 | Meeks | |
| 7,218,392 B2 | 5/2007 | Biellak et al. | |
| 7,227,628 B1 | 6/2007 | Sullivan et al. | |
| 7,227,984 B2 | 6/2007 | Cavan | |
| 7,298,940 B2 * | 11/2007 | Abu-Ageel | 359/489 |
| 2003/0173525 A1 | 9/2003 | Seville | |
| 2005/0122509 A1 | 6/2005 | Backhauss | |
| 2005/0226129 A1 | 10/2005 | Carr | |
| 2006/0245965 A1 | 11/2006 | Wienecke et al. | |
| 2007/0035727 A1 | 2/2007 | Chen et al. | |
| 2007/0067134 A1 | 3/2007 | Borowicz et al. | |

FOREIGN PATENT DOCUMENTS

| | | |
|---|---|---|
| JP | 2000-136916 | 5/2000 |
| JP | 2003-243465 | 8/2003 |
| JP | 2006-294969 | 10/2006 |

OTHER PUBLICATIONS

Article printout from Micromagazine.com website entitled "Meeting Manufacturing Metrology Challenges at 90 nm and Beyond" believed to be dated Aug. 2005.

Article printout from Solid State Technology entitled "Implementation of CVD low-k Dielectrics for High-volume Production" believed to be dated Jan. 2004.

Article entitled "Edge and bevel automated defect inspection for 300mm production wafers in manufacturing" believed to be published in Advanced Semiconductor Manufacturing Conference and Workshop, 2005 IEEE/SEMI Apr. 2005.

Article in Semiconductor International entitled "The Wafer's Edge" dated Mar. 2006.

Article from Augusttech.com entitled "Advanced Macro Inspection Provides Data to Address Blister Defects" believed to be dated Feb. 2005.

Article from NCCAVS User Groups 2005 Annual Symposium entitled "Plasma Etch Polymer: When Good Polymer Goes Bad" dated Oct. 2005.

* cited by examiner

AUTOMATIC WAFER EDGE INSPECTION AND REVIEW SYSTEM

CROSS-REFERENCE TO RELATED APPLICATIONS

This application is a continuation-in-part of U.S. patent application Ser. No. 11/417,297, filed on May 2, 2006, entitled "Substrate Illumination and Inspection System". The disclosure of the above application is incorporated herein by reference.

FIELD

The present disclosure relates to illumination and inspection of a substrate, particularly illumination and inspection of specular surfaces of a silicon wafer edge with diffuse light from a plurality of light sources for enhanced viewing of the wafer edge.

BACKGROUND

The statements in this section merely provide background information related to the present disclosure and may not constitute prior art.

Substrate processing, particularly silicon wafer processing involves deposition and etching of films and other processes at various stages in the eventual manufacture of integrated circuits. Because of this processing, contaminants, particles, and other defects develop in the edge area of the wafer. This includes particles, contaminants and other defects such as chips, cracks or delamination that develop on edge exclusion zones (near edge top surface and near edge back surface), and edge (including top bevel, crown and bottom bevel) of the wafer. It has been shown that a significant percentage of yield loss, in terms of final integrated circuits, results from particulate contamination originating from the edge area of the wafer causing killer defects inside the FQA (fixed quality area) portion of the wafer. See for example, Braun, The Wafer's Edge, Semiconductor International (Mar. 1, 2006), for a discussion of defects and wafer edge inspection methodologies.

Attempts at high magnification inspection of this region of the wafer have been confounded by poor illumination of these surfaces. It is difficult to properly illuminate and inspect the edge area of an in-process wafer. An in-process wafer typically has a reflective specular ("mirror") surface. Attempts at illuminating this surface from a surface normal position frequently results in viewing reflections of surrounding environment of the wafer edge thus making it difficult to visualize defects or distinguish the defects from reflective artifact. Further, the wafer edge area has a plurality of specular surfaces extending from the near edge top surface across the top bevel, the crown, the bottom bevel to the near edge bottom surface. These too cause non-uniform reflection of light necessary for viewing the wafer edge area and defect inspection. In addition, color fidelity to observed films and contrast of lighting are important considerations for any wafer edge inspection system.

Therefore, there is a need for a system that adequately illuminates the edge area of a wafer for inspection. It is important that the system provide for illumination and viewing suitable for a highly reflective surface extending over a plurality of surfaces and for a variety of defects to be observed. The system must provide for efficient and effective inspection of the edge area for a variety of defects.

SUMMARY

Further areas of applicability will become apparent from the description provided herein. It should be understood that the description and specific examples are intended for purposes of illustration only and are not intended to limit the scope of the present disclosure.

The object of the present invention is to provide a color image-based edge defect inspection and review system. It comprises an illuminator to provide uniform diffused illumination across the five wafer edge regions: top near edge surface, top bevel, apex, bottom bevel and bottom near edge surface, an optical imaging subsystem to image a portion of wafer edge supported by a wafer chuck, a positioning assembly to orientate the optical imaging subsystem to the user-defined inspection angle, an eccentricity sensor to actively measure the center offset of a wafer relative to the rotation center of the wafer chuck, a wafer chuck to hold the backside of a wafer onto the supporting pins, a linear stage to move a wafer from its load position to the inspection position, a rotary stage rotates the wafer in a step-and-stop fashion, a control console to provide tool control functions as well as at least the following capabilities: 1) automatic capture of defects of interest with enough sensitivity and speed, 2) automatic defect detection and classification, 3) automatic measurement of wafer edge exclusion width; and 4) automatic report of inspection results to the yield management system of a semiconductor fabrication plant.

In accordance with the present disclosure, a substrate illumination system has a light diffuser with an opening extending at least a portion of its length for receiving an edge of a wafer. The system also comprises a plurality of light sources in proximity to the light diffuser. The system further comprises an optic for viewing the wafer wherein the optic is exterior of the light diffuser and is angled off of the wafer edge surface normal position.

In an additional aspect, the system comprises an illumination control system for independently controlling the plurality of light sources. Individually or by groups or sections, the plurality of lights can be dimmed or brightened. In addition, the plurality of lights can change color, individually or by groups or sections. Yet another aspect of the system comprises a rotation mechanism for rotating the optic from a position facing the top of the wafer to a position facing the bottom of the wafer. In an additional aspect of the system, the plurality of light sources is an LED matrix or alternatively a flexible OLED or LCD. In this aspect the flexible OLED or LCD can act in place of the plurality of lights or in place of both the light diffuser and the plurality of lights. The light sources can also be one or more halogen lamps. The one or more halogen lamps can be coupled to an array of fiber optics.

In yet an additional aspect, the system comprises a method for imaging the specular surface of a substrate. This method comprises, isolating a portion of the substrate in a light diffuser, emitting light onto the specular surface to be imaged and imaging the specular surface with an optic positioned at an angle off the specular surface normal from a position exterior to the light emitter.

DRAWINGS

The drawings described herein are for illustration purposes only and are not intended to limit the scope of the present disclosure in any way.

DETAILED DESCRIPTION

Figure 1:
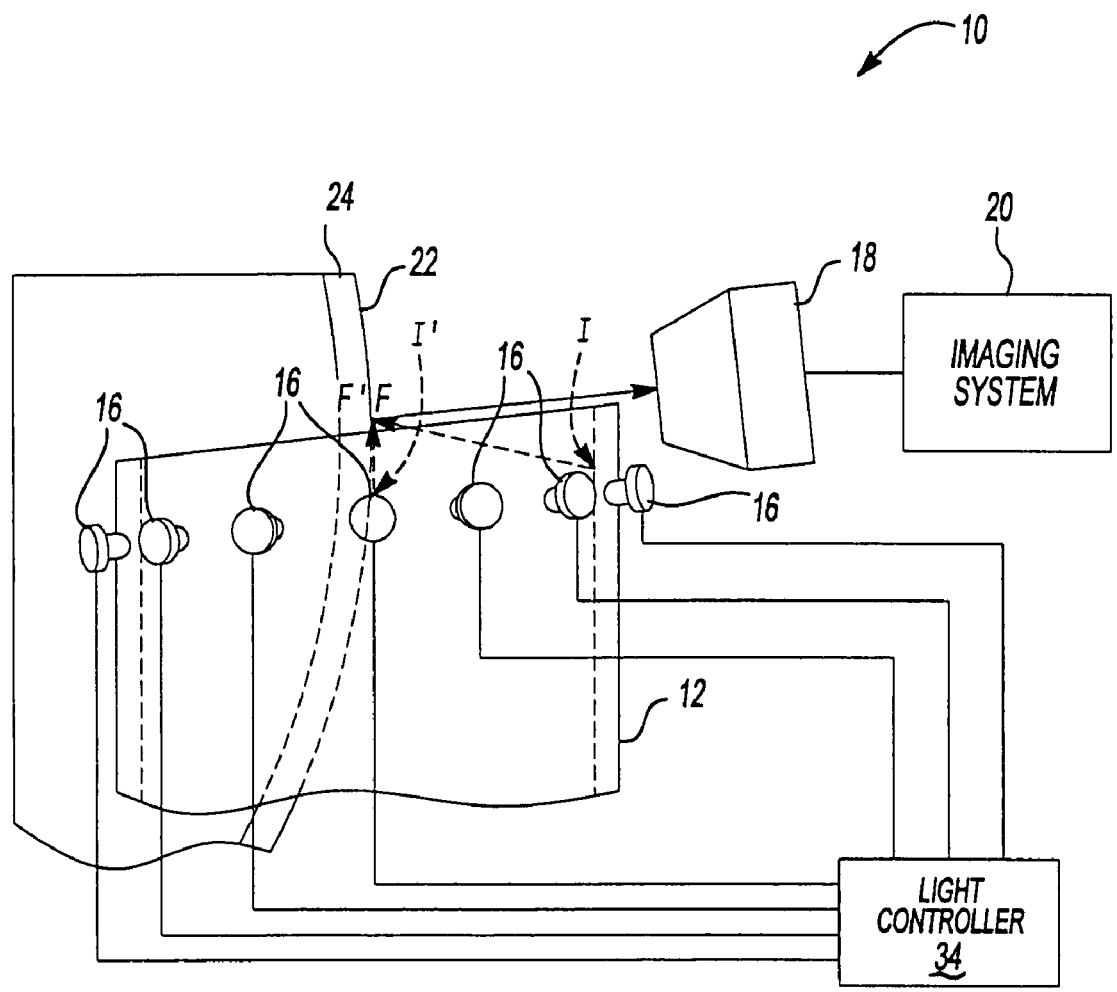
FIG. 1 shows a schematic top view of the substrate illumination system of the present disclosure.

The following description is merely exemplary in nature and is not intended to limit the present disclosure, application, or uses. It should be understood that throughout the drawings, corresponding reference numerals indicate like or corresponding parts and features.

Figure 2:
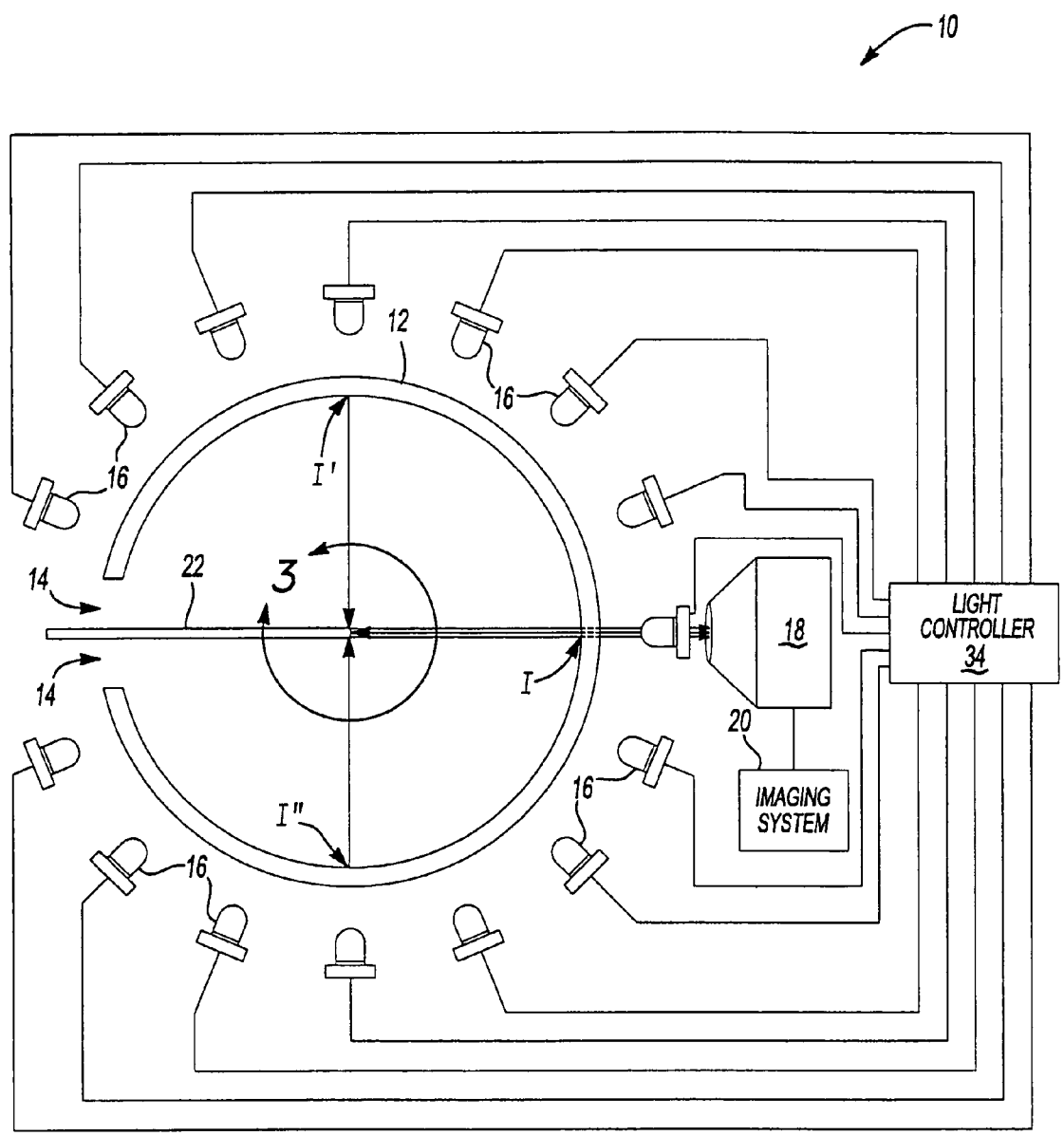
FIG. 2 shows a schematic side view of the system as shown in FIG. 1.
Figure 3:
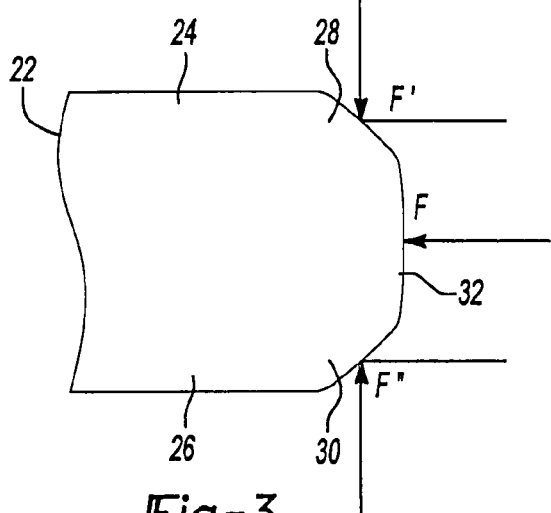
FIG. 3 shows a detailed view of a portion of the view shown in FIG. 2.

Referring to FIGS. 1, 2, and 3 a substrate illumination system 10 (the "system") of the disclosure has a diffuser 12 with a slot 14 along its length and a plurality of lights 16 surrounding its exterior radial periphery. Exterior of the diffuser 12 is an optic 18 that is connected to an imaging system 20 for viewing a substrate 22 as the substrate is held within the slot 14. The plurality of lights 16 are connected to a light controller 34.

The system 10 can be used to uniformly illuminate for brightfield inspection of all surfaces of an edge area of the substrate 22 including, a near edge top surface 24, a near edge bottom surface 26, a top bevel 28, a bottom bevel 30 and a crown 32.

The optic 18 is a lens or combination of lenses, prisms, and related optical hardware. The optic 18 is aimed at the substrate 22 at an angle off a surface normal to the crown 32 of the substrate 22. The angle of the optic 18 advantageously allows for preventing a specular surface of the substrate 22 from reflecting back the optic 18 whereby the optic 18 "sees itself." The viewing angle is typically 3 to 6 degrees off normal. Some optimization outside of this range is possible depending on illuminator alignment relative to the substrate 22 and the specific optic 18 configuration.

The imaging system 20 is for example a charge-coupled device (CCD) camera suitable for microscopic imaging. The imaging system 20 may be connected to a display monitor and/or computer (not shown) for viewing, analyzing, and storing images of the substrate 22.

Diffuser 12 is formed of a translucent material suitable for providing uniform diffuse illumination. The diffuser 12 may be formed of a frosted glass, a sand blasted quartz or a plastic or the like, where light passing through it is uniformly diffused. In a preferred embodiment, the diffuser 12 is a circular cylinder as illustrated. Diffuser 12 may be an elliptic cylinder, generalized cylinder, or other shape that allows for surrounding and isolating a portion of a substrate 22 including the substrate 22 edge. The slot 14 in the diffuser 12 extends for a suitable length to allow introduction of the substrate 22 into the diffuser 12 far enough to provide uniform illumination of the edge area and to isolate the edge area from the outside of the diffuser 12.

Importantly, the interior of the diffuser 12 serves as a uniform neutral background for any reflection from the specular surface of the substrate 22 that is captured by the optic 18. Thus, the optic 18 while looking towards focal point F on the specular surface of the crown 32 images (sees) the interior of the diffuser 12 at location I. Similarly, the optic 18 looking towards focal points F' and F" on the specular surfaces of the top bevel 28 and bottom bevel 30 respectively, images the interior of the diffuser 12 at locations I' and I".

The angle of the optic 18 in cooperation with the diffuser 12 prevents reflective artifacts from interfering with viewing the plurality of specular surfaces of the edge area of the substrate 22. Instead, and advantageously, a uniform background of the diffuser 12 interior is seen in the reflection of the specular surfaces of the substrate 22.

The plurality of lights 16 is a highly incoherent light source including an incandescent light. In a preferred embodiment, the plurality of lights 16 is an array of LEDs. Alternatively, a quartz halogen bulb can be the light source with fiber optics (not shown) used to distribute light of this single light source radially around the diffuser 12. In another preferred embodiment the plurality of lights 16 is an array of fiber optics each coupled to an independent, remotely located quartz tungsten halogen (QTH) lamp.

The plurality of lights 16 is preferably a white light source to provide the best color fidelity. In substrate 22 observation, color fidelity is important because of film thickness information conveyed by thin film interference colors. If the substrate 22 surface is illuminated with light having some spectral bias, the thin film interference information can be distorted. Slight amounts of spectral bias in the light source can be accommodated by using filters and/or electronic adjustment (i.e., camera white balance).

In operation, a substrate 22, for example, a wafer is placed on a rotatable chuck (not shown) that moves the edge of the wafer into the slot 14 of the diffuser 12. The light controller 34 activates in suitable brightness the plurality of lights 16 for providing uniform illumination of the edge area of the wafer. The wafer is viewed through the imaging system 20 via the optic 18 and inspected for defects. The wafer may be automatically rotated or manually rotated to allow for selective viewing of the wafer edge. Thus, observation of the wafer edge for defects is facilitated and is unhindered by a specular surface of the wafer.

Figure 4:
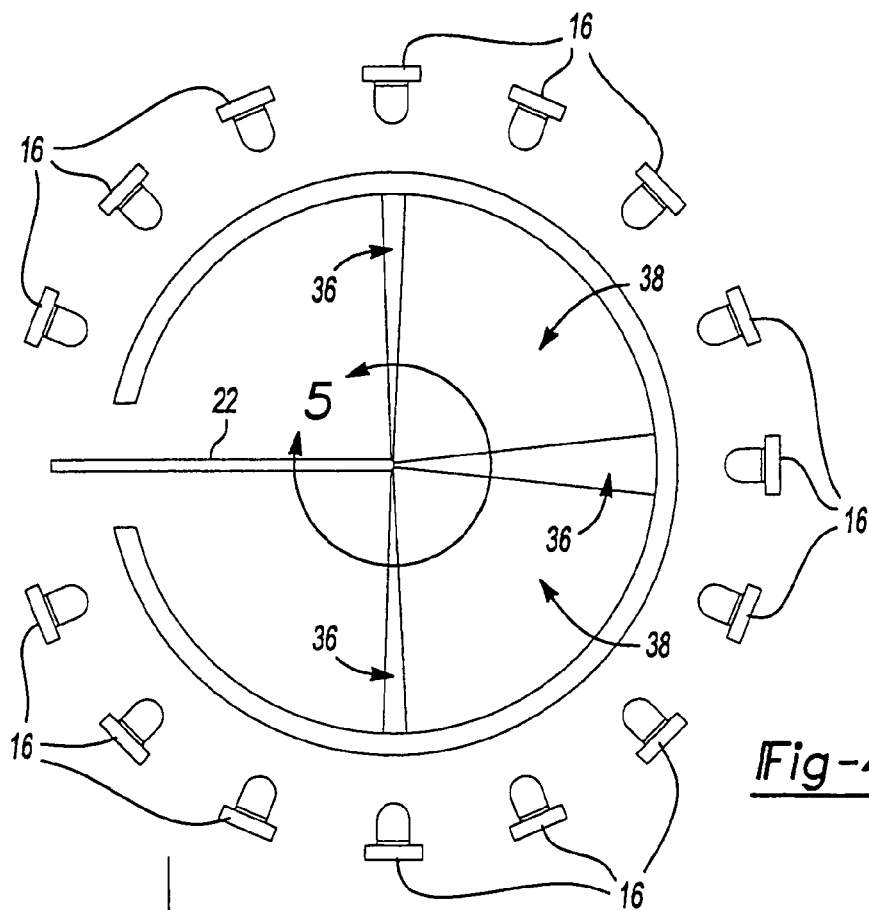
FIG. 4 shows a schematic side view of an alternative embodiment of the substrate illumination system.
Figure 5:
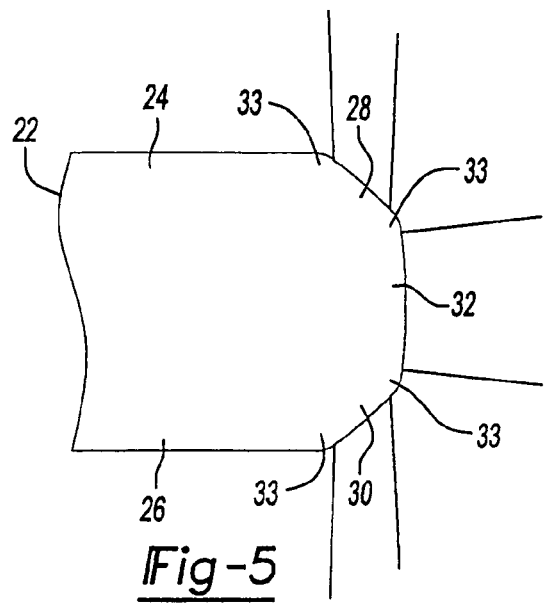
FIG. 5 shows a detailed view of a portion of the view shown in FIG. 4.

With added reference to FIGS. 4 and 5, in an embodiment of the system 10 the plurality of lights 16 are individually controlled by the light controller 34. In this embodiment light controller 34 is a dimmer/switch suitable for dimming individually or in groups a plurality of lights. Alternatively, light controller 34 can be the type as disclosed in U.S. Pat. No. 6,369,524 or 5,629,607, incorporated herein by reference. Light controller 34 provides for dimming and brightening or alternatively turning on/off individually or in groups each of the lights in the plurality of lights 16.

The intensity of a portion of the plurality of lights 16 is dimmed or brightened to anticipate the reflective effect of specular surfaces that are inherent to the substrate 22, particularly at micro locations along the edge profile that have very small radii of curvature. These micro locations are the transition zones 33 where the top surface 24 meets the top bevel 28 and the top bevel meets the crown 32 and the crown meets the bottom bevel 30 and the bottom bevel 30 meets the bottom surface 26.

An example of addressable illumination is illustrated in FIGS. 4 and 5 where higher intensity illumination 36 is directed to a top bevel 28, crown 32 and bottom bevel 30 while lower intensity illumination 38 is directed to the transition zones 33 in between. With this illumination configuration, the image of these transition zones 33 are seen illuminated with similar intensity as compared to the top bevel 28, crown 32 and bottom bevel 30.

Further, addressable illumination is useful to accommodate intensity variation seen by the optic 18 due to view factor of the substrate 22 edge area. Some portions of the substrate 22 edge area have a high view factor with respect to the illumination from the diffuser 12 and consequently appear relatively bright. Other portions with low view factor appear relatively dark. Addressable illumination allows mapping an intensity profile onto the wafer surface that allows for the view factor variation and provides a uniformly illuminated image. The required intensity profile can change with viewing angle change of the optic 18.

Addressability of the illumination or its intensity can be accomplished in a number of ways. One embodiment is to locate independently controllable light-emitting diodes (LEDs) around the outside of the diffuser 12 consistent with the plurality of lights 16. Another alternative is to employ a small flexible organic light-emitting diode (OLED), liquid crystal display (LCD) or other micro-display module. Such modules are addressable to a much greater degree than an LED matrix. In this embodiment the flexible OLED, LCD or other micro-display module can replace both the plurality of lights 16 and the diffuser 12. For example, a flexible OLED can both illuminate and have a surface layer with a matte finish suitable for acting as a diffuser and neutral background for imaging. Further, the flexible OLED can be formed into a suitable shape such as a cylinder. Examples of a suitable OLED are disclosed in U.S. Pat. Nos. 7,019,717 and 7,005,671, incorporated herein by reference.

Further, those modules can also provide programmable illumination across a broad range of colors including white light. Color selection can be used to highlight different thin films and can be used in combination with part of an OLED, for example, emitting one color while another part of the OLED emits another color of light. In some cases it can be beneficial to use only part of the light spectrum, for example, to gain sensitivity to a film residue in a given thickness range. This is one mode of analysis particularly applicable to automatic defect classification. One analysis technique to detect backside etch polymer residue preferentially looks at light reflected in the green portion of the spectrum. Thus, this embodiment of the system 10 provides for a suitable color differential based inspection of the substrate 22.

Figure 6:
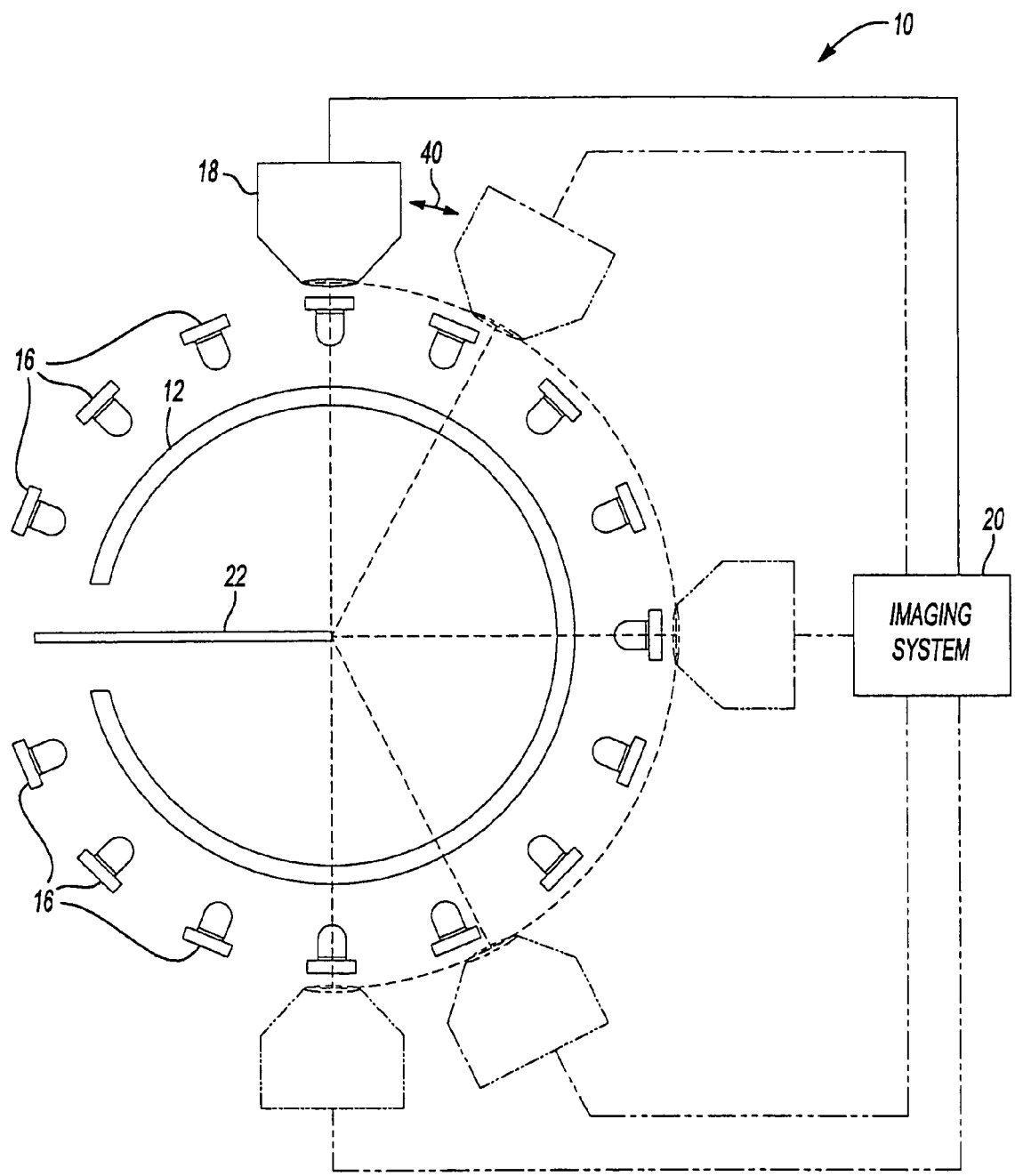
FIG. 6 shows a schematic side view of another alternative embodiment of the substrate illumination system.

Now referring to FIG. 6, in another embodiment of the system 10, the optic 18 is rotatable in a radial direction 40 around the substrate 22 at a maintained distance from a center point of the substrate 22 edge. The optic 18 is rotatable while maintaining the angle of the optic 18 relative to surface normal of the substrate 22 edge. This allows for focused imaging of all regions of the substrate 22 surface, including the top surface 24, bottom surface 26, top bevel 28, bottom bevel 30 and crown 32. The rotating optic 18 can also include the imaging system 20 or consist of a lens and a CCD camera combination or can be a subset of this consisting of moving mirrors and prisms. This embodiment provides the additional advantage of using one set of camera hardware to view the substrate 22 rather than an array of cameras.

Figure 7:
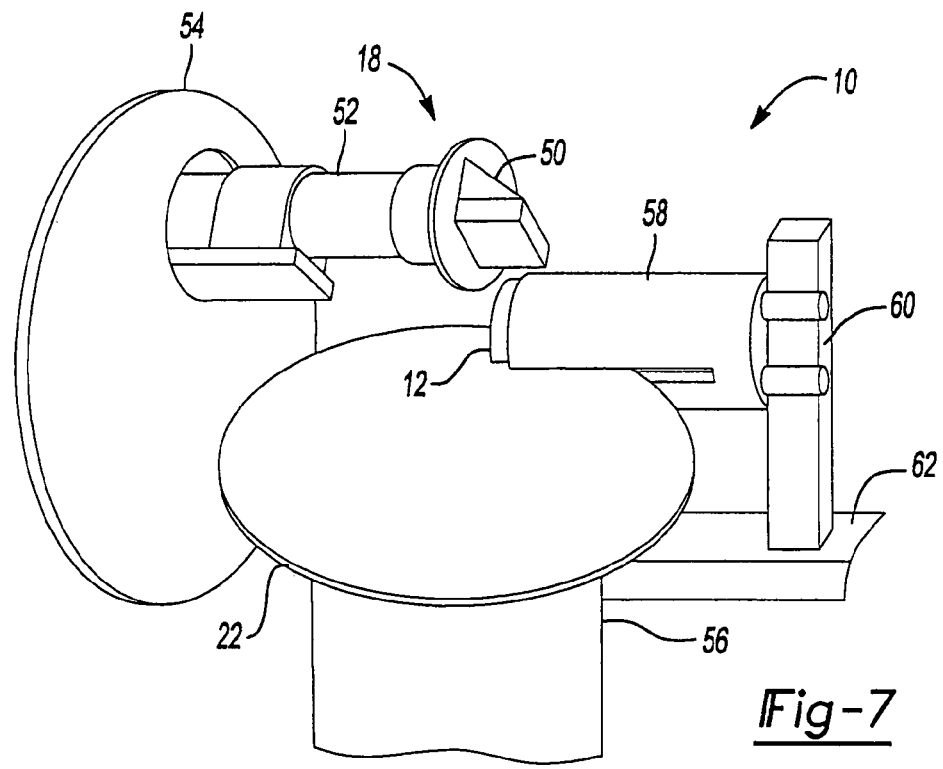
FIG. 7 shows a perspective view of yet another embodiment of the substrate illumination system.
Figure 8:
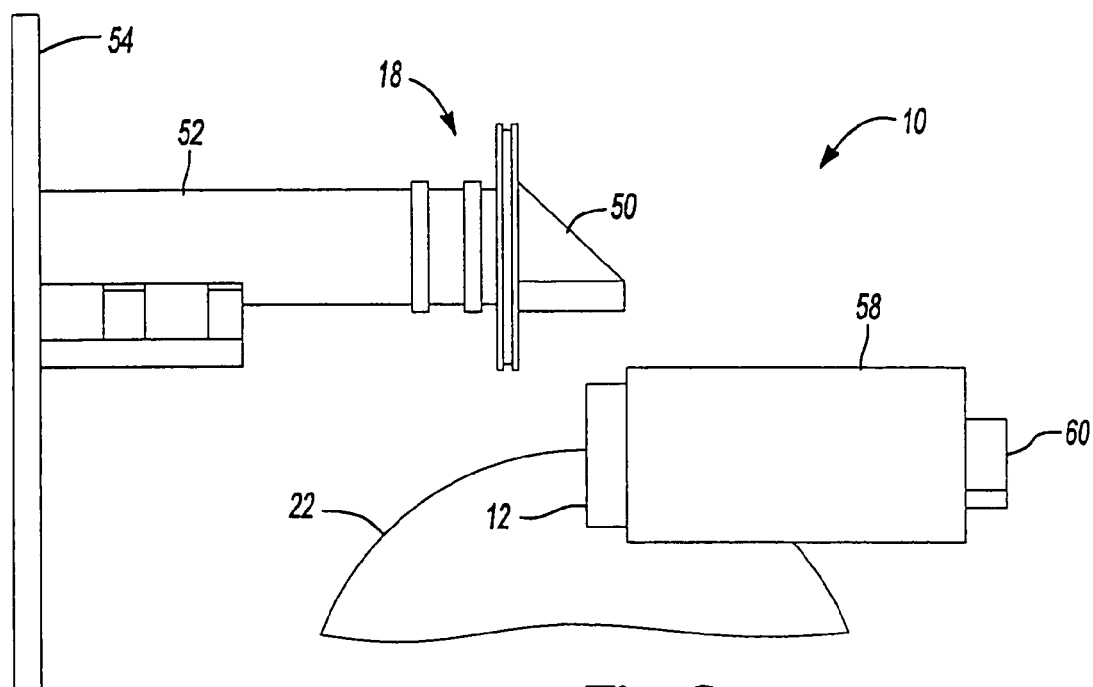
FIG. 8 shows a top plan view of the alternative embodiment of the substrate illumination system as shown in FIG. 7.

Now referring to FIGS. 7 and 8, in another embodiment of the system 10, the optic 18 includes a fold mirror 50 and a zoom lens assembly 52. The optic 18 is connected to a rotatable armature 54 for rotating the optic 18 radially around the edge of the substrate 22 (as similarly discussed in relation to FIG. 6). The substrate 22 is retained on a rotatable chuck 56. The diffuser 12 is housed in an Illumination cylinder 58 that is retained on a support member 60 connected to a support stand 62.

The operation of this embodiment of the system 10 is substantially the same as described above with the additional functionality of radially moving the optic 18 to further aid in inspecting all surfaces of the edge of the substrate 22. Further, the substrate 22 can be rotated either manually or automatically by the rotatable chuck 56 to facilitate the inspection process.

Figure 9:
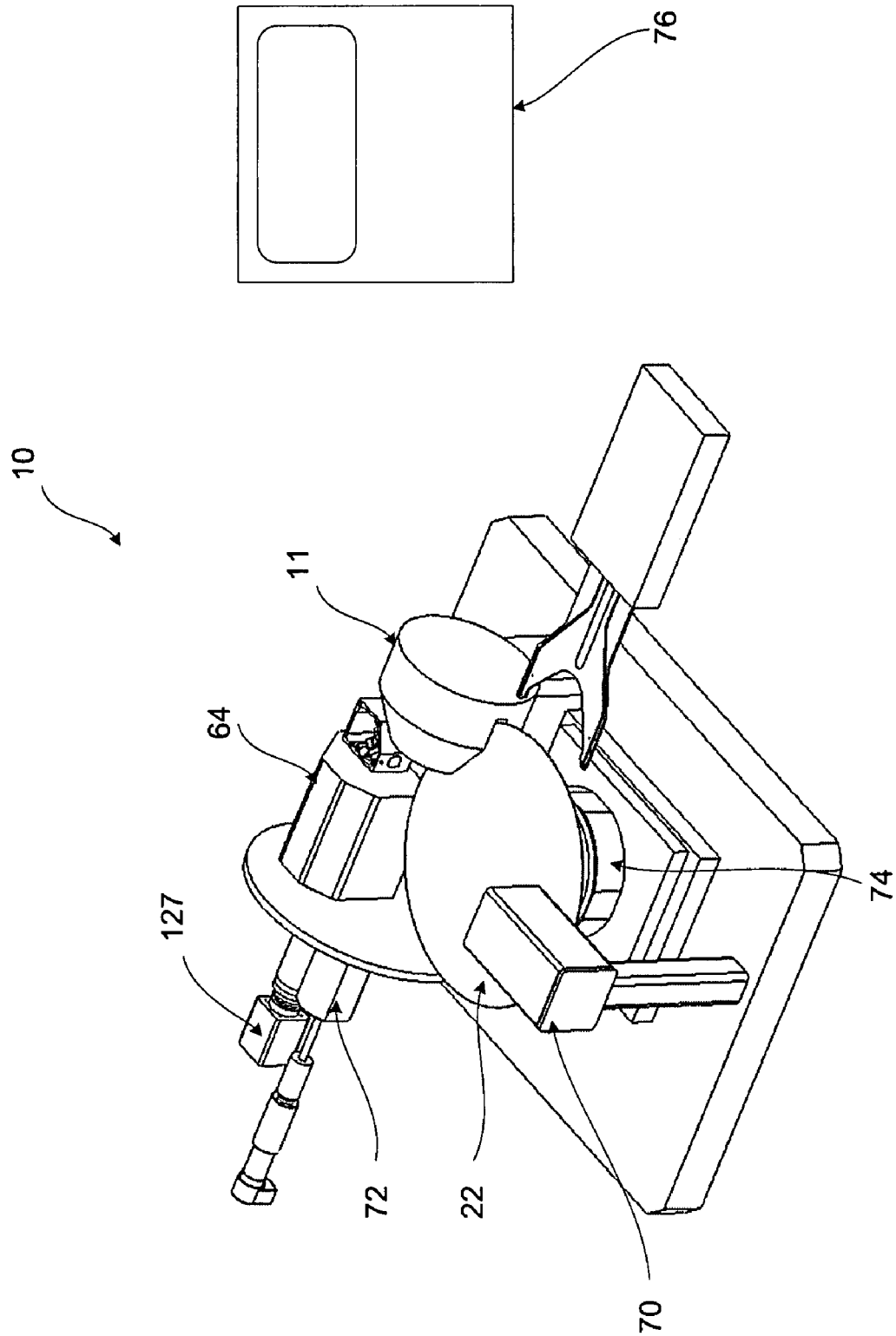
FIG. 9 shows a perspective view of a wafer edge inspection and review system of the present disclosure.

Referring to FIG. 9 an automatic wafer edge inspection and review system 10 consists of an illuminator 11, an optical imaging subsystem 64, a wafer supporting chuck 66 (not shown), a positioning assembly 68, an eccentricity sensor 70, a linear stage 72, a rotary stage 74, and a control console 76. The eccentricity sensor 70 is used to provide eccentricity data to the controller to allow the controller to positionally adjust the substrate 22 with respect to the imaging system 64. Optionally, data from the eccentricity sensor 70 can be used to adjust the optics system to ensure uniformity of the image and focus as opposed to or in conjunction with the supporting chuck 66.

Figure 10:
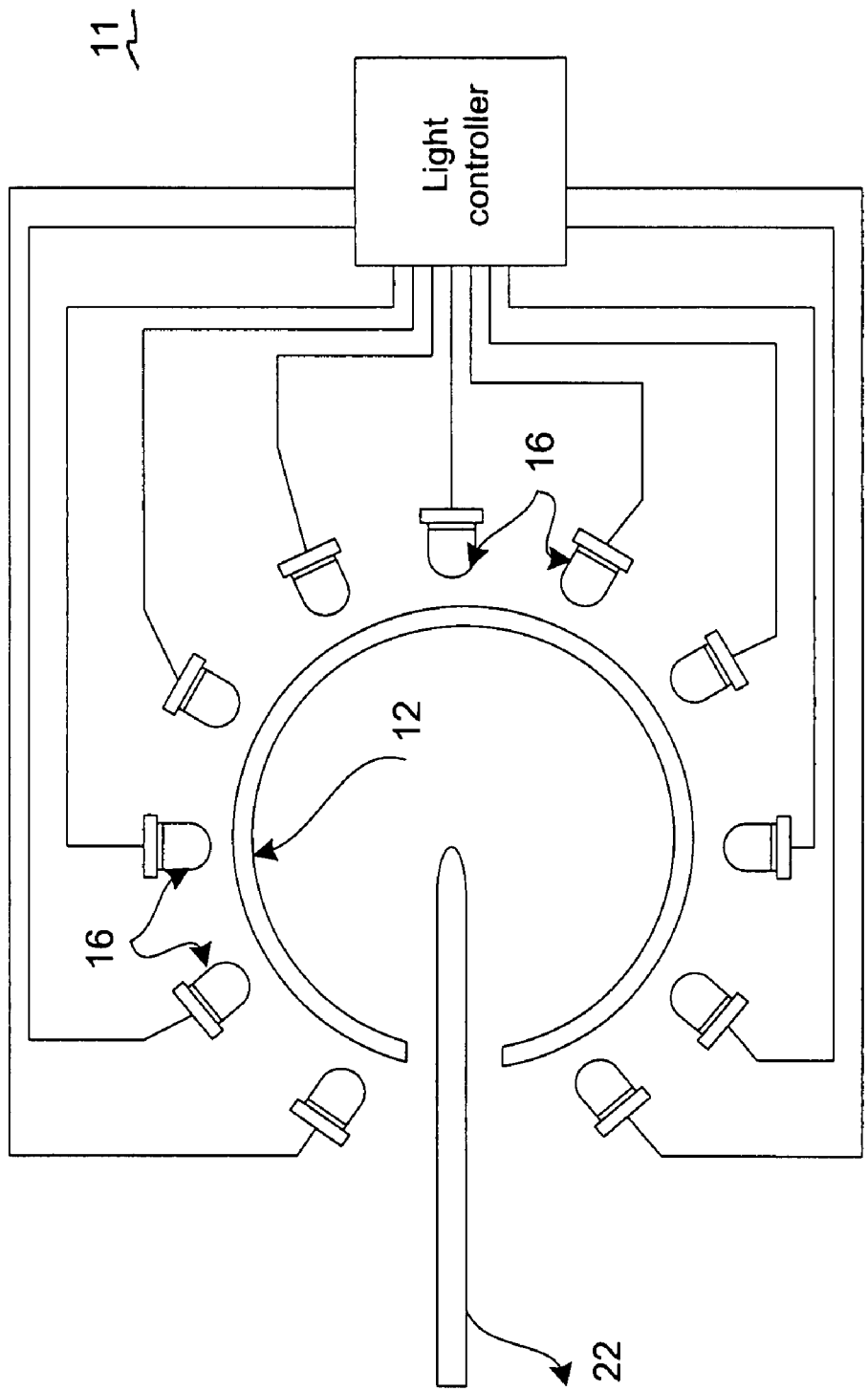
FIG. 10 shows a cross section view of the illuminator shown in FIG. 9.
Figure 11:
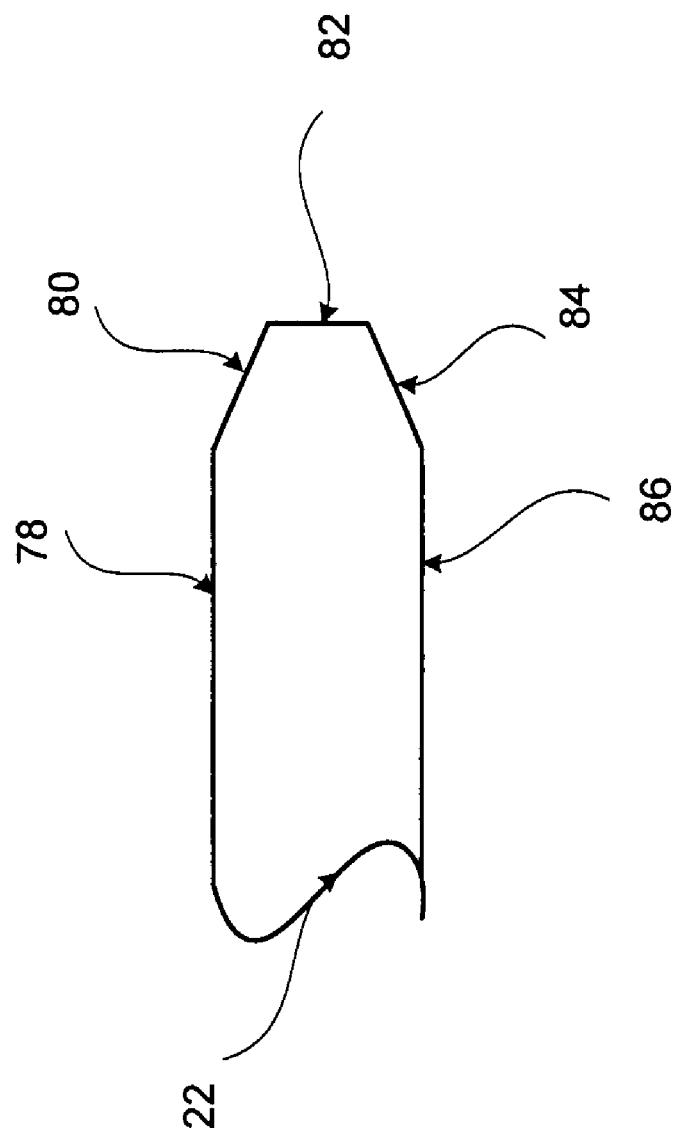
FIG. 11 shows a enlarged cross section view of the wafer edge regions.

Referring to FIG. 10 and as described above, the illuminator 11 provides uniform illumination across the five wafer edge regions: top near edge surface 78, top bevel 80, apex 82, bottom bevel 84, and bottom near edge surface 86, as show in FIG. 11. It is also envisioned the illuminator 11 can vary the intensity or color of the illumination depending upon the expected defect or substrate region. Additionally, the illuminator 11 can individually illuminate different regions of the wafer. The light controller received input from the system controller 76.

Figure 12:
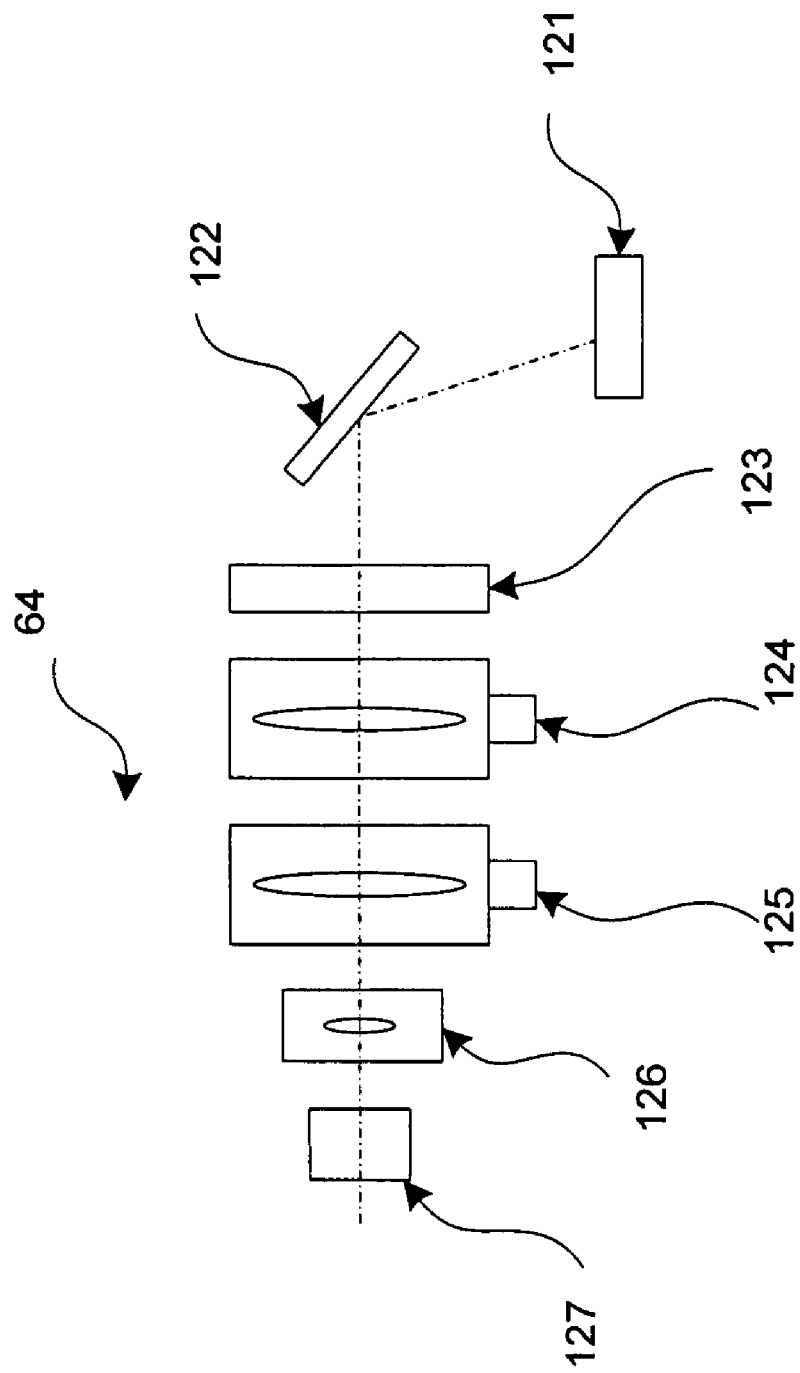
FIG. 12 shows a schematic view of the optical imaging subsystem shown in FIG. 9.
Figure 13:
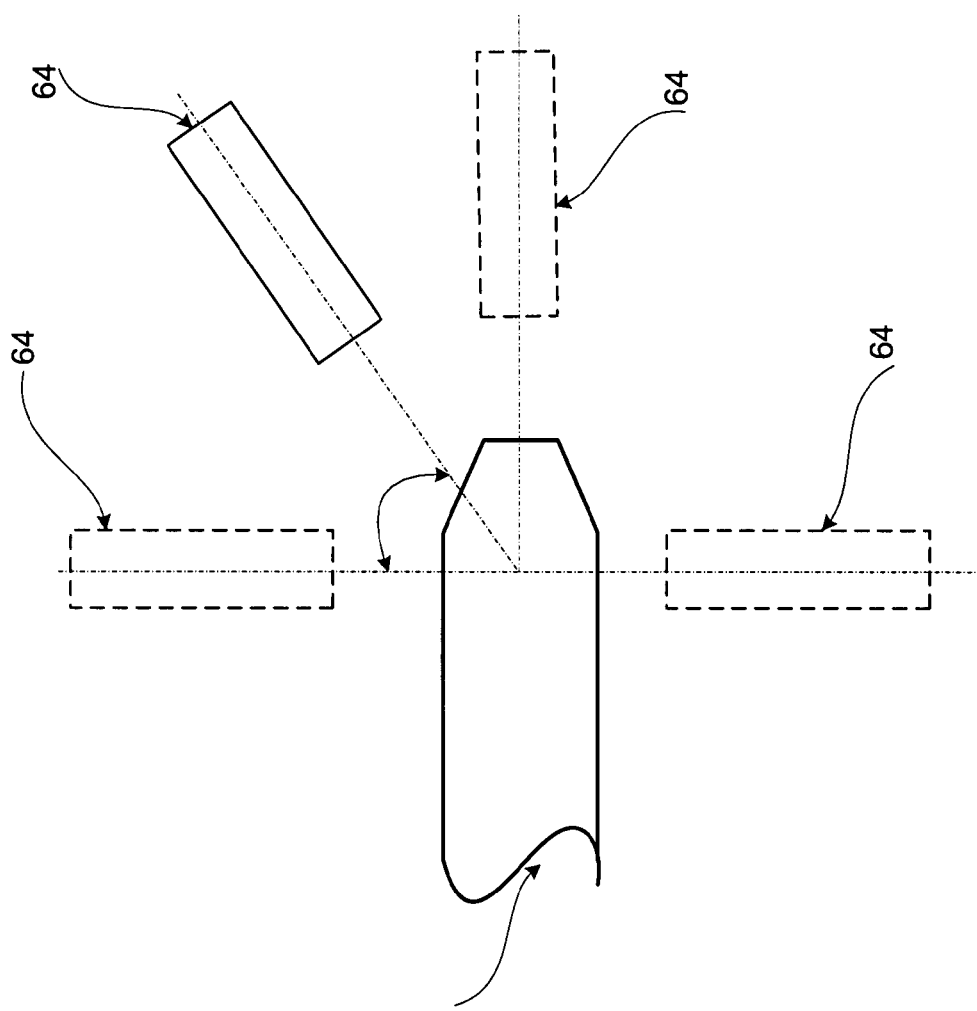
FIG. 13 shows the inspection angles of the optical imaging subsystem shown in FIG. 9.

Referring to FIG. 12, the optical imaging subsystem 64 has a filter 121, a mirror 122, an attachment objective lens 123, a motorized focus lens 124, a motorized zoom lens 125, and a magnifier lens 126, and a high resolution area scan color camera 127. The motorized focus lens 124 automatically or manually sets best focus position before starting automatic inspection and during the review process. The filter 121 can be a polarizer, or optical filter which allows the passage of predetermined frequencies.

Figure 14:
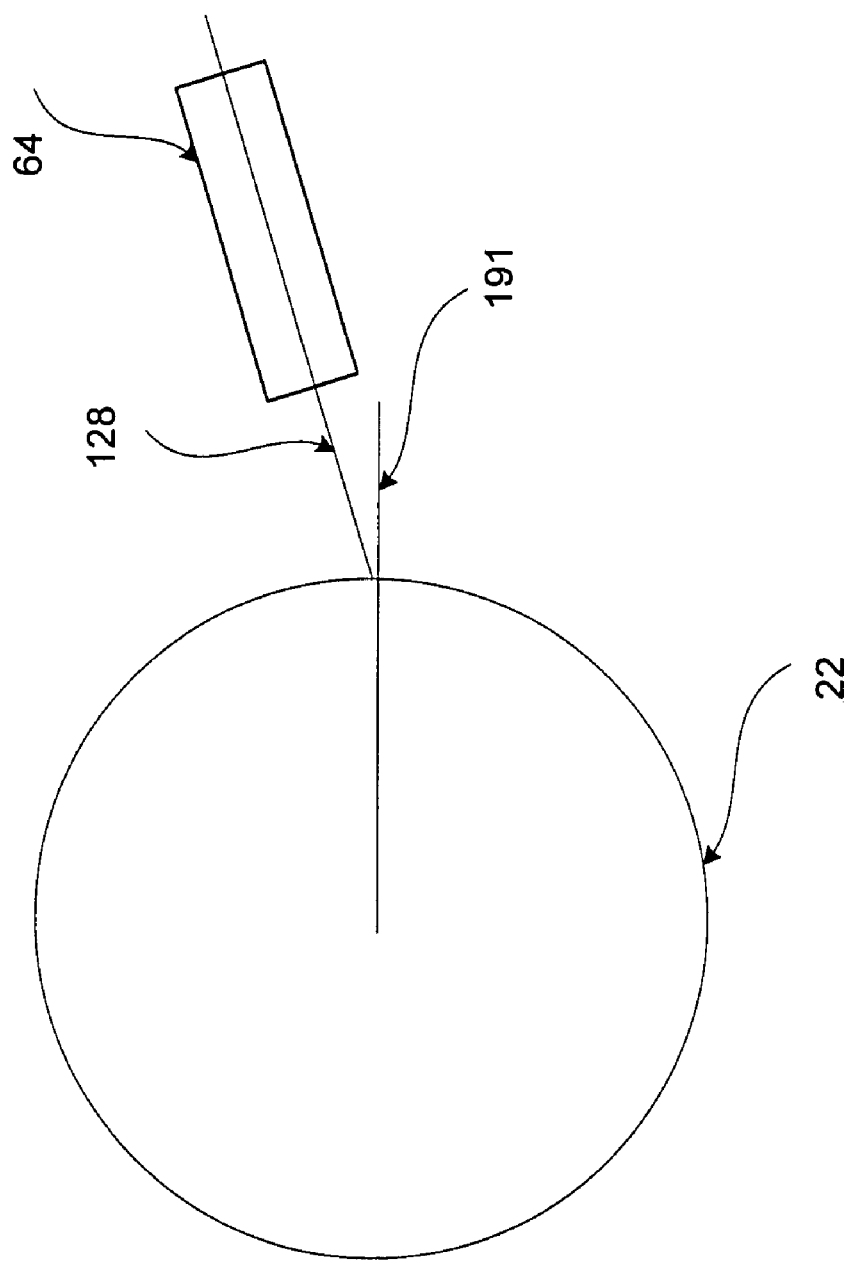
FIG. 14 shows the angle between the principal axis of the optical imaging subsystem and the normal of the edge portion.
Figure 15:
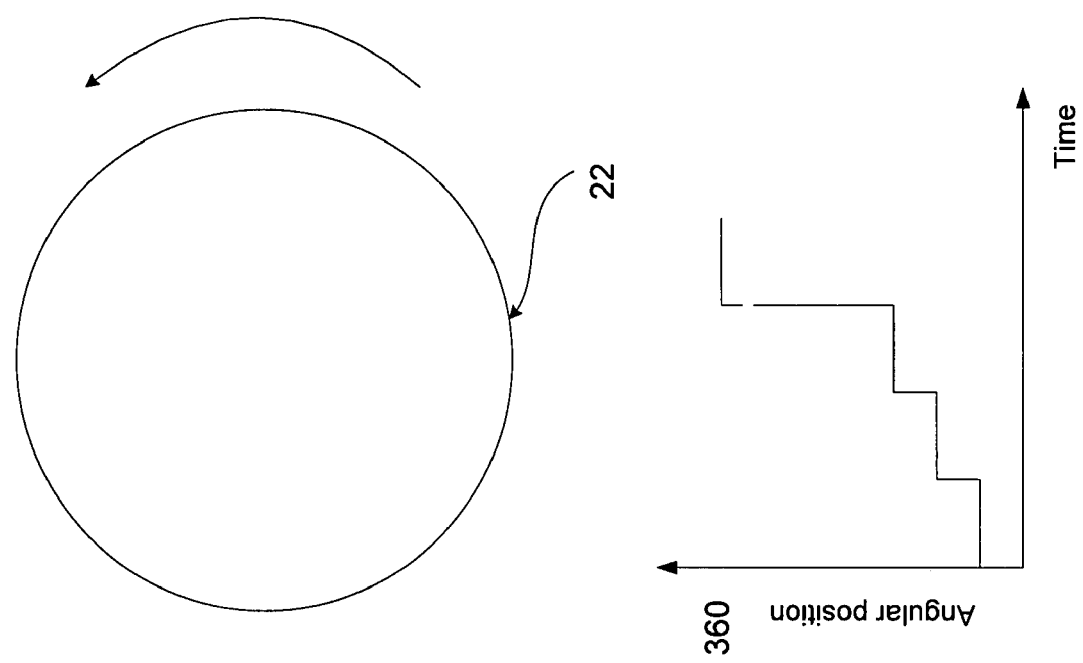
FIG. 15 illustrates the step-and-stop angular motion of a wafer.

The motorized zoom lens 125 can be configured in the low magnification range for inspection purpose and high magnification range for review purpose. As shown in FIG. 14, the positioning assembly 68 orientates the optical imaging subsystem 64 to the predefined inspection angle 51. To improve the image, the optical imaging subsystem 64 is orientated in such a way that its principal axis 128 preferably is kept from the normal direction 191 of the wafer edge portion under inspection. The linear stage 72 moves the wafer from its load position to the inspection position, and also performs the eccentricity compensation to bring the wafer always to the best focus position during the image acquisition period. While the rotary stage 74 rotates the substrate 22 along the circumference direction in a step-and-stop manner, as shown in FIG. 15, it is envisioned a continuous rotation of the wafer is possible.

The control console 76 controls the system 10 via the tool control software. In this regard, the console 76 controls the motion of linear stage 72 and rotary stage 74, positioning the assembly 68 to the user-defined inspection angle. The controller further presets the magnification of the motorized zoom lens 125 and focus position of the motorized focus lens 124, initializing the image acquisition timing and other essential functions to complete the automatic inspection of a wafer using user-predefined routines. The control console 76 also displays the acquired images and runs the defect inspection and classification software, reporting the results files to a factory automation system.

Referring generally to FIG. 9 which shows the operation of one embodiment, a substrate 22 is picked up from a FOUP (not shown) or an open cassette (not shown) in the equipment front end module (not shown) by the transportation robot arm 27, placed onto the rotational table of the aligner (not shown). The aligner detects the center of the substrate 22 as well as its notch, aligns the wafer to the center axis of the rotational table. After alignment is completed, the transport robot arm 27 picks up the substrate 22 from the aligner, places it onto the wafer chuck (not shown) of the inspection and review system 10.

Then, the wafer is rotated and the eccentricity sensor 70 starts to measure the eccentricity of the wafer relatively to the spin center of the rotary stage 74. The eccentricity information is fed back to the control console 76. At the same time, the positioning assembly 68 moves the optical imaging subsystem 64 to the routine inspection angle. Then the linear stage 72 moves the substrate 22 to the inspection position from the load position. The rotary stage 74 starts to move forward one step (routine-defined angle) and stops completely. The illuminator 11 is turned on, and the camera 127 takes an image of the portion of the wafer edge within the field of view of the optical imaging system 64. After completion, the rotary stage 74 rotates one more step, settling down completely. The linear stage 72 moves the substrate 22 to the best focus position based on the eccentricity data stored in the control console 76. During the movement of the stage 72, the control console 76 downloads the previous images from the camera to the onboard memory and the hard disk media. Then, the camera 127 takes the second picture of the wafer edge. The above steps are repeated until the region of interest or the whole circumference of the substrate 22 is imaged.

If the system is set to inspect the edge regions of substrate 22 in more than one inspection angles, the control console 76 moves the positioning assembly 68 to another inspection angle, repeating the steps described above. The images of the edge of the substrate 22 at the new inspection angle are recorded until all inspection angles of interest are covered.

After the completion of imaging all the predefined edge regions of substrate 22, the transport robot arm 27 picks the substrate 22 from the inspection chamber, and place it back to a FOUP or a cassette in the equipment front end module.

Figure 16:
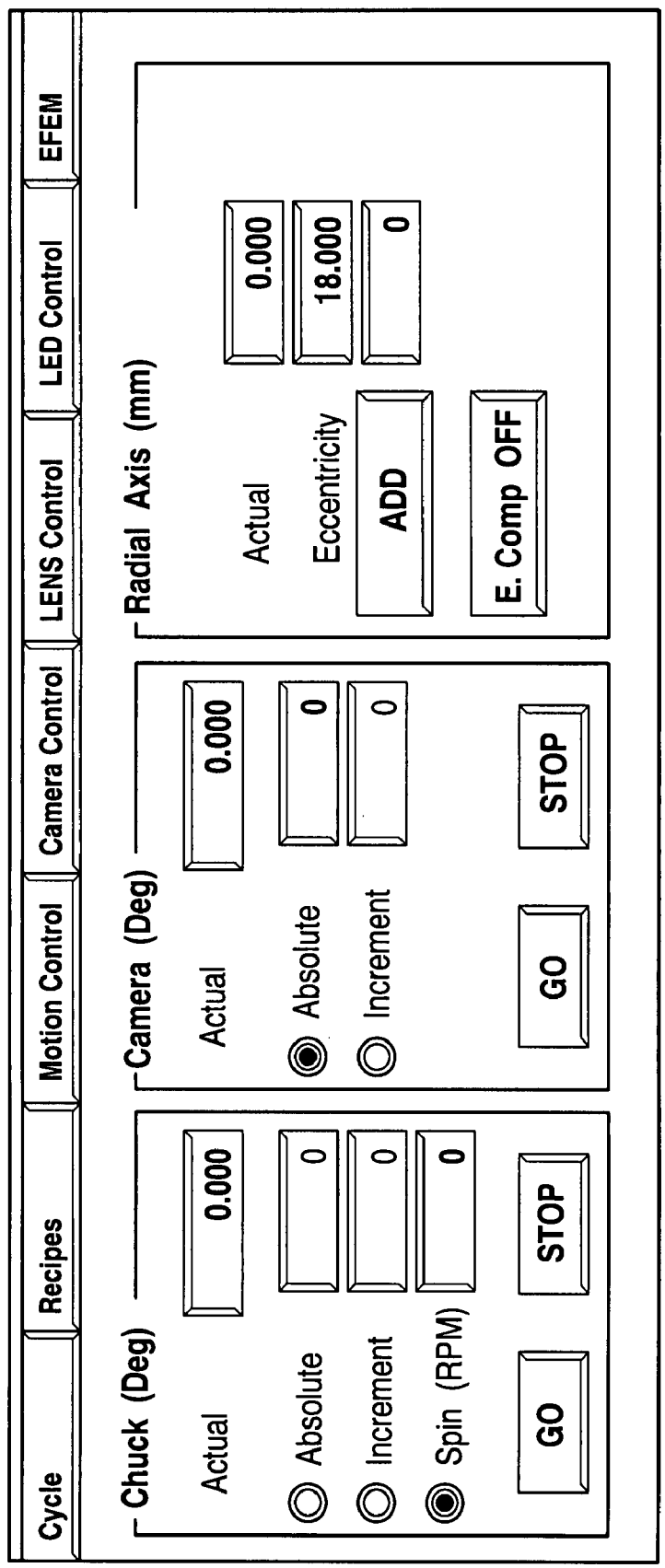
FIG. 16 shows a user interface for semi-automated defect review.
Figure 17:
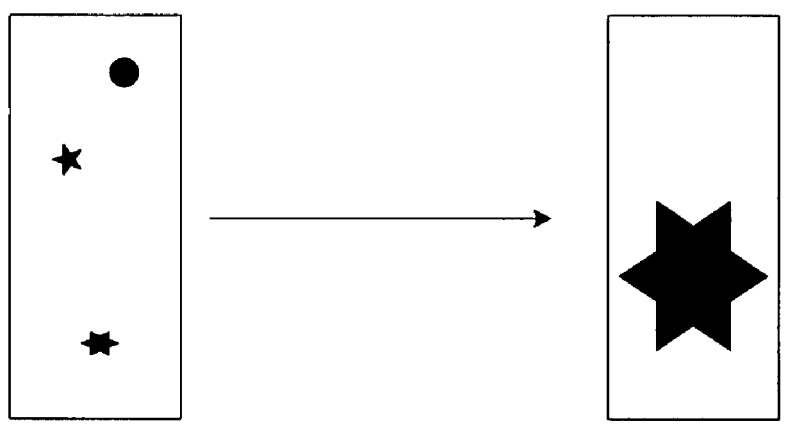
FIG. 17 shows the process to review a specific defect of interest.

While the system 10 takes pictures of the edge of substrate 22, the inspection and classification software installed in control console 76 processes the raw images, detects the defects of interest, classifies them into different classes or category and outputs to the results files. To review a specific defect found by the system 10, the location and the inspection angle of the specific defect can be retrieved from the results files. As shown in FIG. 16, an operator inputs this information to the review system setup area of tool control software in the control console 76. The control console 76 automatically moves the substrate 22 and the positioning assembly 68 to the predetermined positions, locates the specific defect of interest. Then, the user adjusts the magnification of the motorized zoom lens 125 to the desired value, focusing on the defect by adjusting the position of the motorized focus lens 124. The operator can now review the details of the defect on the display and record its image to storage devices of the control console 76.

Figure 18:
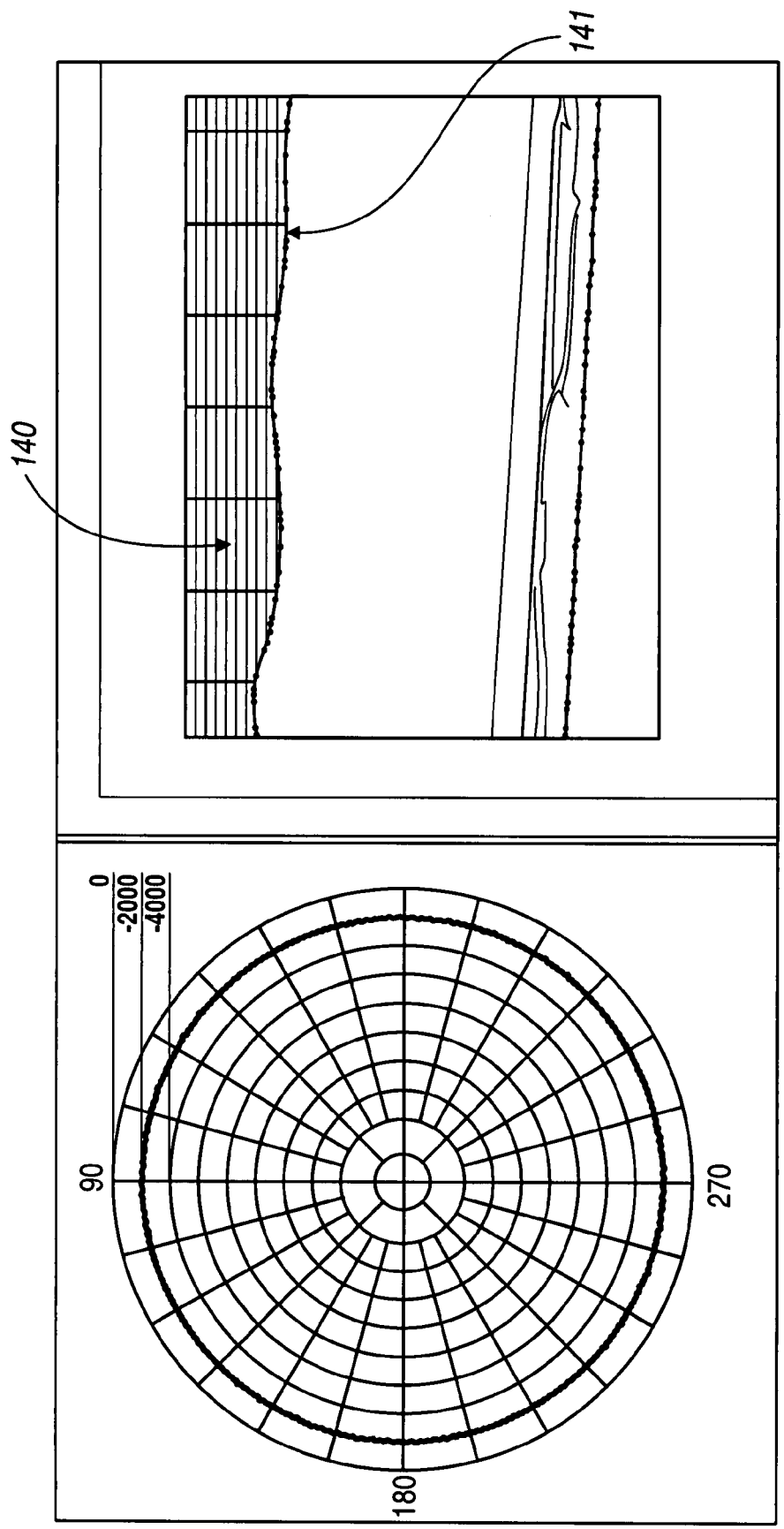
FIGS. 18 and 19 show an example of edge exclusion measurement.

Referring to FIGS. 9 and 18, the system is used to measure the cut line 141 of the edge bead removal of a film layer 140. The positioning assembly 68 moves the optical imaging subsystem 64 and the area scan camera 127. In this position, the top near edge surface of the substrate 22 with the cut line 141 is visible within the field of view. The motorized focus lens 124 is set to the position where the image is under best focus. The rotary stage 74 starts to move forward one step (predefined angle) and stops completely. The illuminator 11 is turned on, and the camera 127 takes an image of a portion of the near top edge surface including the cut line 141. Then, the rotary stage 74 moves one more step, settling down completely. While the stage is in motion, the control console 76 downloads the image from the camera 127 to the onboard memory and the hard disk media. Upon completion, the camera 127 takes the second picture. The above steps are repeated until the whole cut line along the circumference of the substrate 22 is completely imaged and recorded onto onboard memory and the hard disk media.

During operation, the control console 76 processes the recorded images to calculate the profile of the cut line 141 as well as the following parameters: the center disposition from the wafer center, mean edge exclusion distance, the standard deviation, and the peak-to-peak variation. The results are output to the results file with predefined format.

Figure 19:
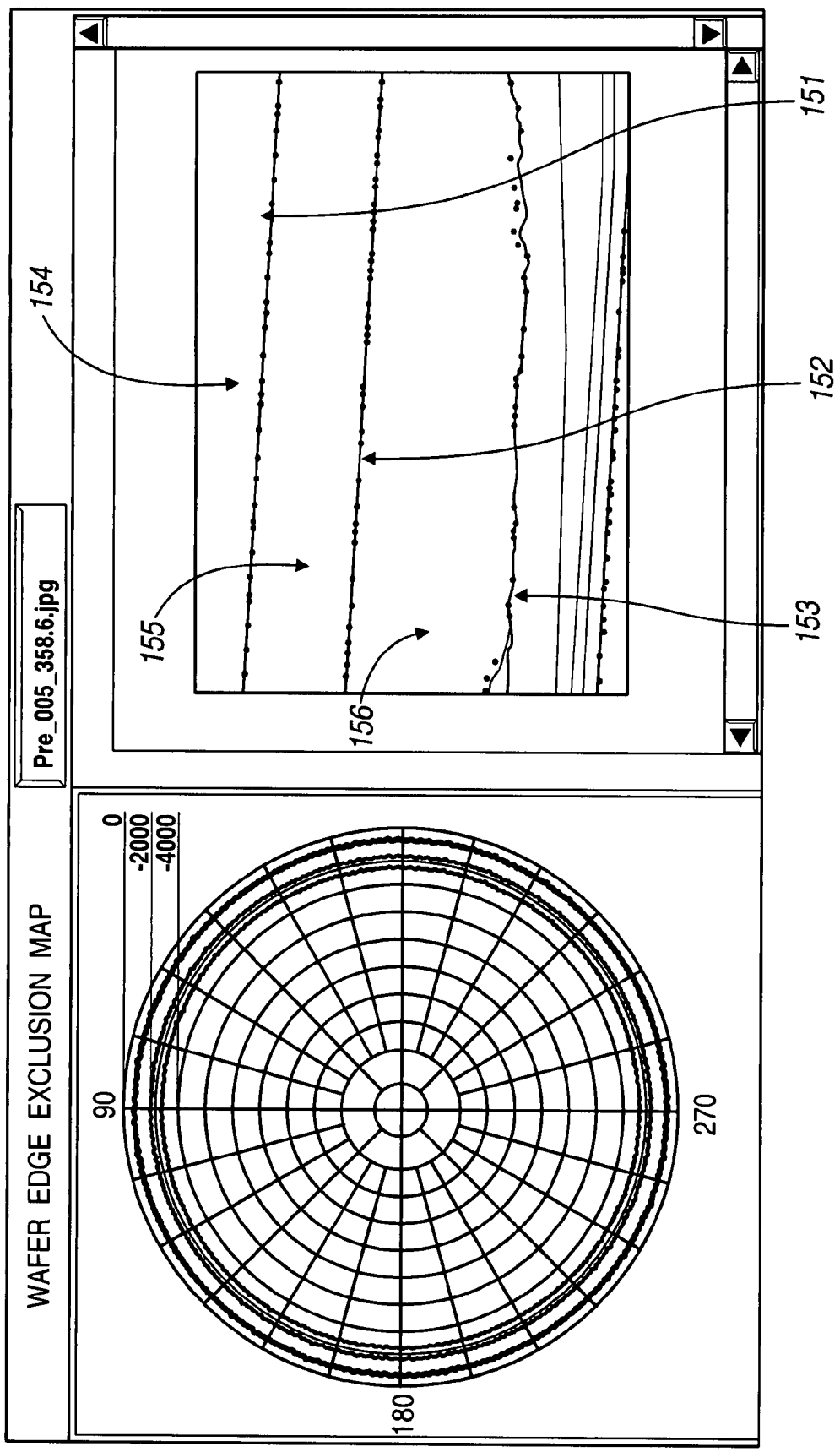

As shown in FIGS. 9 and 19, the wafer edge inspection and review system 10 can be used to measure multiple cut lines, for example, 151, 152, and 153 of multiple film layers 154, 155, and 156. The positioning assembly 68 moves the optical imaging subsystem 64 and the area scan camera 127 to a position so that the top near edge surface of the substrate 22 with the cut lines 151, 152 and 153 is within the field of view. The motorized focus lens 124 is set to the position where the image is under best focus. The rotary stage 74 starts to move forward one step and stops completely. The illuminator 11 is turned on, and the camera 127 takes an image of a portion of the near top edge surface including the cut lines 151, 152 and 153. Then, the rotary stage 74 moves a second step, settling down completely. While the rotary stage is in motion, the control console 76 downloads the picture from the camera 127 to the onboard memory and the hard disk media. Upon completion, the camera 127 takes the second picture. The above steps are repeated until the whole cut lines along the circumference of the substrate 22 are completed imaged and recorded onto onboard memory and the hard disk media.

It should be appreciated that while the embodiments of the system 10 are described in relation to an automated system, a manual system would also be suitable. This includes a hybrid automated/manual inspection with automated or manual defect classification as described in U.S. Provisional Patent Application 60/964,163, filed Aug. 9, 2007, entitled "Apparatus and Method for Wafer Edge Defects Detection" and U.S. Provisional Patent Application 60/964,149, filed Aug. 9, 2007, entitled "Apparatus and Method for Wafer Edge Exclusion Measurement", both incorporated herein by reference. This also includes automated inspection in conjunction with automated wafer handling including robotic wafer handling with wafers delivered via FOUP or FOSB.

Thus, a cost effective yet efficient and effective system is provided for illuminating and inspecting the plurality of surfaces of the edge area of a substrate 22 and providing high quality imaging of the inspected surfaces while avoiding the interference associated with specular surfaces. The system provides for improving quality control of wafer processing through edge inspection with the intended benefit of identifying and addressing defects and their causes in the IC manufacturing process with resulting improvement in yield and throughput.

What is claimed is:

1. An automatic wafer edge inspection and review system comprising:
   an illuminator configured to provide diffused illumination across the top near edge surface, top bevel, apex, bottom bevel, and bottom near edge surface;
   an optical imaging subsystem to image a portion of the wafer edge;
   a positioning assembly to orientate the optical imaging subsystem to an inspection angle;
   an eccentricity sensor to actively measure the center offset of a wafer edge relative to the rotation center of the wafer chuck; and
   a wafer chuck to hold the backside of a wafer.

2. The system of claim 1, wherein the optical imaging subsystem further comprises:
   an optical filter to cut off certain wavelength spectrum;
   a mirror;
   an objective lens;
   a motorized focus lens to provide routine-defined focus adjustment;
   a motorized zoom lens;
   a magnifier lens; and
   a high resolution area scan color camera to image a portion of the wafer edge.

3. The system of claim 1, wherein the illuminator comprises:
   a cylindrical light diffuser having a slit extending at least a portion of its length for receiving an edge portion of a wafer;
   a plurality of light sources exterior or interior to the cylindrical light diffuser; and
   an intensity controller for independently controlling the plurality of light sources.

4. The system of claim 1, wherein the optical imaging subsystem is orientated in such a way that its principal axis is always kept away from the normal direction of the wafer edge portion under inspection.

5. The system of claim 1 further comprising:
   a rotary stage which rotates the wafer in a step-and-stop fashion; and
   a control console to provide tool control functions, image display, defect inspection, defect classification and edge exclusion measurement capabilities.

6. The system of claim 5, wherein the eccentricity sensor measures the eccentricity of a wafer and provides a signal to the control console.

7. The system of claim 5, wherein the rotary stage rotates the wafer along the circumference direction in a step-and-stop manner.

8. The system of claim 6, wherein the linear stage performs the eccentricity compensation, and brings the wafer to a best focus position based on the signal from the eccentricity sensor.

9. The system of claim 5, wherein the control console performs automatic defect inspection and classification, automatic measurement of edge bead removal cut lines and semi-automated defect review.

10. The system of claim 2, wherein the filter is a polarizer.

11. An automatic wafer edge inspection and review system of claim 1, wherein the wafer chuck is a pin-chuck and the wafer is held on top of a plurality of pins by vacuum.

12. A wafer edge illumination and inspection system comprising:
    a light diffuser having a slit extending at least a portion of its length for receiving a portion of a wafer including a portion of the wafer edge;
    a plurality of light sources in proximity to the light diffuser; and
    an optical imaging subsystem for viewing the wafer wherein the optic is exterior of the light diffuser, and is positioned at an angle off a wafer edge surface normal, wherein the optical imaging subsystem further comprises an optical filter to cut off certain wavelength spectrum, a mirror, an objective lens, a motorized focus lens to provide routine-defined focus adjustment, a motorized zoom lens, a magnifier lens, a rotation mechanism for rotating the optic about an axis parallel to the wafer radially relative to a center point of the wafer edge region to allow imaging of a wafer top near edge surface, top bevel, apex, bottom bevel and bottom near edge surface, and a high resolution area scan color camera to image a portion of the wafer edge.

13. The wafer edge illumination and inspection system of claim 12 further comprising:
    an illumination control system for independently controlling the plurality of light sources.

14. The wafer edge illumination and inspection system of claim 12, wherein the light diffuser is a quartz tube.

15. The wafer edge illumination and inspection system of claim 12, wherein the plurality of light sources is an LED matrix.

16. The LED matrix of claim 15, wherein each LED is independently controllable.

17. The wafer edge illumination and inspection system of claim 12, wherein the plurality of light sources is an array of fiber optics each coupled to an independent remotely located lamp.

18. The array of fiber optics of claim 17, wherein each lamp is independently controllable.

19. The wafer edge illumination and inspection system of claim 12, wherein the plurality of light sources is an LCD matrix.

20. The wafer edge illumination and inspection system of claim 12, wherein the plurality of light sources is a flexible OLED.

21. A substrate imaging system for imaging a specular surface of a substrate, the system comprising:
    a light diffuser housing having an opening for receiving a portion of the substrate wherein the interior of the light diffuser housing is a uniform neutral background to a specular surface being imaged wherein the light diffuser housing extends from over a top surface of the wafer to adjacent an edge of the wafer and under a bottom surface of the wafer;
    an optical subsystem angled off a surface normal of the substrate area to be imaged wherein the optical lens is exterior to the light diffuser, wherein the optical subsystem comprise, a mirror, an objective lens, a motorized focus lens to provide routine-defined focus adjustment, a motorized zoom lens to provide both inspection and review functions, a magnifier lens, and a high resolution area scan color camera to image a portion of wafer edge;

a light source disposed in the light diffuser housing; and an eccentricity sensor to actively measure the center offset of a wafer edge relative to the rotation center of the wafer chuck.

22. The substrate imaging system of claim 21, wherein the light source is coupled to a fiber optic for directing light from the light source to a plurality of locations of the light diffuser housing.

23. The substrate imaging system of claim 21, wherein the light source is one selected from the group of an LED matrix, LCD matrix, and OLED.

24. The substrate imaging system of claim 21 further comprising:

a light controller for controlling the color and brightness of the light source.

25. The substrate imaging system of claim 15, wherein the light source is one selected from the group of an LED matrix, LCD matrix, and OLED, wherein the light diffuser housing is a covering attached to the light source.

* * * * *